United States Patent [19]

Iglewski et al.

[11] Patent Number: 4,470,924

[45] Date of Patent: Sep. 11, 1984

[54] **NONTOXIC, IMMUNOLOGICALLY CROSSREACTIVE TOXIN A PROTEIN FROM *PSEUDOMONAS AERUGINOSA***

[76] Inventors: Barbara M. Iglewski, 4746 SW. Lowell Ct., Portland, Oreg. 97221; Stanley J. Cryz, Jr., Stamtachgasse 6, Bolligen, Switzerland, 3065

[21] Appl. No.: 335,993

[22] Filed: Dec. 30, 1981

[51] Int. Cl.[3] .................... C07G 7/00; A61K 39/104; C12P 21/00; C12N 1/20

[52] U.S. Cl. .................................. 260/112 R; 424/88; 424/92; 435/68; 435/253

[58] Field of Search .............. 260/112 R; 424/88, 92; 435/253, 68

[56] References Cited

U.S. PATENT DOCUMENTS 4,285,936 8/1981 Pier et al. ............................ 424/92

OTHER PUBLICATIONS

Chemical Abstracts, vol. 91, p. 166, Abst. No. 84300n, 1979.

Chemical Abstracts, vol. 90, p. 143, Abst. No. 133715, 1979.

Iglewski, B., et al., Proc. Nat. Acad. Sci., vol. 72, pp. 2284–2288, 1975.

Cryz, Jr., et al., Proc. Natl. Acad. Sci., vol. 77, pp. 7199–7203, Dec. 1980.

*Primary Examiner*—Blondel Hazel

*Attorney, Agent, or Firm*—Kolisch, Hartwell, Dickinson & Anderson

[57] ABSTRACT

A nontoxic, immunologically crossreactive toxin A protein produced by a PAO-PR1 mutant strain of *Pseudomonas aeruginosa.* The protein, in activated form, has substantially no adenosine diphosphate-ribosylating activity, and is nontoxic to cells known to be susceptible to the parent PAO-1 strain of *Pseudomonas aeruginosa* from which strain PAO-PR1 was derived. The nontoxic toxin A protein is immunologically indistinguishable from, and has a molecular weight similar to, native toxin A protein produced by the PAO-1 strain.

5 Claims, 2 Drawing Figures

NONTOXIC, IMMUNOLOGICALLY CROSSREACTIVE TOXIN A PROTEIN FROM *PSEUDOMONAS AERUGINOSA*

This invention was supported by generous grants from the National Institutes of Health, Institute of Allergy and Infectious Diseases.

The following publications are referred to by corresponding number in this application:

1. Feigin, R. D., and Shearer, W. T.: Opportunistic infections in children. II. In the compromised host. J. Pediatrics 87:677–694, 1975.
2. Reynolds, H. Y., Levine, A. S., Wood, R. E., Zierdt, C. H., Dale, D. G., and Pennington, J. E.: *Pseudomonas aeruginosa* infections: persisting problems and current research to find new therapies. Annals. Int. Med. 82:819–831, 1975.
3. Cicmanec, J. F., and Holder, I. A.: Growth of *Pseudomonas aeruginosa* in normal and burned skin extract: role of extracellular proteases. Infect. Immun. 24:477–483, 1979.
4. Morihara, K., Tsuzuki, H., and Oda, K.: Protease and elastase of *Pseudomonas aeruginosa:* inactivation of humas plasma $_1$-proteinase inhibitor. Infect. Immun. 24:188–193, 1979.
5. Kreger, A. S., and Gray, L. D.: Purification of *Pseudomonas aeruginosa* protease and microscopic characterization of pseudomonal protease-induced rabbit corneal damage. Infact. Immun. 19:630–648, 1978.
6. Pavlovskis, O. R., Pollack, M., Callahan, L. T., III, and Iglewski, B. H.: Passive protection by antitoxin in experimental *Pseudomonas aeruginosa* burn infections. Infect. and Immun. 18:596–602, 1977.
7. Cross, A. S., Sadoff, J. C., Iglewski, B. H., and Sokol, P. A.: Evidence for the role of toxin A in the pathogenesis of human infection with Pseudomonas. J. Infect. Dis. 142:538–546, 1980.
8. Ohman, D. E., Burns, R. P., and Iglewski, B. H.: Corneal infections in mice with toxin A and elastase mutants of *Pseudomonas aeruginosa.* J. Infect. Dis. 142:547–555, 1980.
9. Iglewski, B. H., and Kabat, D.: NAD-dependent inhibition of protein synthesis by *Pseudomonas aeruginosa* toxin. Proc. Soc. Nat. Acad. Sci. USA 72:2284–2288, 1975.
10. Iglewski, B. H., Liu, P. V., and Kabat, D.: Mechanism of action of *Pseudomonas aeruginosa* exotoxin A: ADP-ribosylation of mammalian elongation factor 2 in vitro and in vivo. Infect. Immun. 15:138–144, 1972.
11. Chung, D. W., and Collier, R. J.: Enzymatically active peptide from the adenosine diphosphateribosylating toxin of *Pseudomonas aeruginosa.* Infect. Immun. 16:832–841, 1977.
12. Middlebrook, J. L., and Dorland, R. B.: Response of cultured mammalian cells to exotoxins of *Pseudomonas aeruginosa* and *Corynebacterium diphtheriae* differential cytotoxicity. Can. J. Microbiol. 23:183–189, 1977.
13. Liu, P. V.: Exotoxins of *Pseudomonas aeruginosa.* I. Factors that influence the production of exotoxin A. J. Infect. Dis. 128:506–513, 1973.
14. Holloway, B. W., Krishnapillai, V., and Morgan, A. F.: Chromosomal genetics of Pseudomonas. Microbiol. Rev. 43:73–102, 1979.
15. Bjorn, M. J., Iglewski, B. H., Ives, S. K., Sadoff, J. C., and Vasil, M. L.: Effect of iron on yields of exotoxin A in cultures of *Pseudomonas aeruginosa* PA-103. Infect. Immun. 19:785–791, 1978.
16. Cryz, S. J., Friedman, R. L., and Iglewski, B. H.: Isolation and characterization of a *Pseudomonas aeruginosa* mutant producing a nontoxic, immunologically crossreactive toxin A protein. Proc. Nat. Acad. Sci. USA 77:7199–7203, 1980.
17. Iglewski, B. H., and Sadoff, J. C.: Toxin inhibitors of protein synthesis: Production, purification and assay of *Pseudomonas aeruginosa* toxin A. In, L. Grossman and K. Moldave (eds.) Methods of Enzymology. Academic Press, New York, Vol. 60, pps. 353–361, 1979.
18. Murphy, J. R., Bucha, P., and Teng, M.: Determination of *Corynebacterium diphtheriae* toxinogenicity by a colorimetric tissue culture assay. J. Clin. Microbiol. 7:91–96, 1978.
19. March, S. C., Parikh, I., and Cuatrecasas, P.: A simplified method for cyanogen bromide activation of agarose for affinity chromatography. Annal. Biochem. 60:149–152, 1974.
20. Laemmli, U. K.: Cleavage of structural proteins during the assembly of the head of bacteriophage T4. Nature (London) 227:680–685, 1970.
21. Leppla, S. H., Martin, D. C., and Muehl, L. A.: The exotoxin of *Pseudomonas aeruginosa.* A proenzyme having an unusual mode of activation. Biochem. Biophys. Res. Commun. 81:532–538, 1978.
22. Vasil, M. L., Kabat, D., and Iglewski, B. H.: Structure-activity relationships of an exotonix of *Pseudomonas aeruginosa.* Infect. Immun. 16:353–361, 1977.
23. Liu, P. V. and Hsieh, H.: Exotoxins of *Pseudomonas aeruginosa.* III. Characteristics of antitoxin A. J. Infect. Dis. 128:520–526, 1973.
24. Snell, K., I. A. Holder, S. A. Leppla and Saelinger, C. B.: Role of exotoxin and protease as possible virulence factors in experimental infections with *Pseudomonas aeruginosa.* Infect. Immun. 19:839–845, 1978.
25. Pollack, M., Callahan, L. T., III, and Taylor, N. S.: Neutralizing antibody to *Pseudomonas aeruginosa* exotoxin in human sera: Evidence for in vivo toxin production during infections. Infect. Immun., 1976.
26. Pollack, M., Taylor, N. S., and Callahan, L. T., III. Exotoxin production by clinical isolates of *Pseudomonas aeruginosa* Infect. Immun. 15:776–780, 1977.
27. Pollack, M. S. and Young, L. S.: Protective activity of antibodies to exotoxin A and lipopolysaccharide at the onset of *Pseudomonas aeruginosa* septicemia in man. J. Clin. Invest. 63:276–286, 1979.

BACKGROUND OF THE INVENTION

*Pseudomonas aeruginosa* is a major cause of infection in compromised hosts (1, 2). *P. aeruginosa* synthesizes a number of extracellular products, including alkaline protease, elastase and toxin A, which are believed to be involved in the pathogenesis of *P. aeruginosa* infections (3–8). Toxin A, the most toxic of these products, is a potent inhibitor of eucaryotic protein synthesis. The toxin has been shown to catalyze the transfer of the adenosine diphosphate-ribosyl (ADPR) moiety of nicotinamide adenosine dinucleotide (NAD) onto eucaryotic elongation factor 2, thereby rendering this factor nonfunctional in protein synthesis (9–12).

Studies with animal models suggest that toxin A is an important factor in *P. aeruginosa* infections. In the burned mouse model, toxin A antitoxin therapy provided significant protection when mice were challenged with *P. aeruginosa* (6). A specific toxin A-deficient mutuant of *P. aeruginosa* strain PAO-1, termed PAO-T1, exhibited a markedly reduced virulence in a mouse corneal infection model (8) and in the chronic rat lung model. Furthermore, a study of patients with *P. aeruginosa* bacteremia showed a correlation between a rise in toxin A antibody level and survival (13).

These findings have prompted efforts aimed at developing an efficacious toxin A toxoid vaccine. One approach has been to treat toxin A by chemical means in an attempt to produce a toxoid protein product which is nontoxic, and yet retains its immunogenicity. However, to date these attempts have not been successful in that the chemical treatment either fails to produce an irreversible reduction in the cytotoxicity of the toxin A protein, or the immunogenicity of the protein is severely compromised.

SUMMARY OF THE INVENTION

A nontoxic, immunologically crossreactive toxin A protein from *Pseudomonas aeruginosa* is obtainable from the novel microorganism of the strain *Pseudomonas aeruginosa* PAO-PR1 having the identifying characteristics of ATCC 39018. The nontoxin toxin A protein is produced by growing PAO-PR1 on a suitable medium. The protein is purified by batch binding on DEAE-cellulose, ammonium sulfate precipitation, and antibody affinity chromotography. The purified protein has a molecular weight of about 66,000 daltons and is immunologically indistinguishable, based on its immunodiffusion and radioimmunoassay characteristics, from native (toxic) toxin A protein. The nontoxic protein has no substantial ADPR-transferase activity in its activated form.

Strain PAO-PR1 from which the nontoxic toxin A protein is derived was developed from a parent *Pseudomonas aeruginosa* strain PAO-1 by exposing the parent strain to a mutagenic agent. Mutant bacterial strains in the mutagenized PAO-1 culture which were nontoxic to living cells known to be susceptible to the products of PAO-1 strain were isolated. Strain PAO-PR1 was selected from among the isolated nontoxic mutant strains.

These and other objects and features of the present invention will become more fully apparent when the following detailed description of a preferred embodiment of the invention is read in connection with the accompanying drawings, wherein:

FIG. 1 shows the agar gel immunodiffusion pattern of native and nontoxic toxin A protein precipitated with toxin A antitoxin; and FIG. 2 shows the radioimmunoassay for toxin A competition for antitoxin binding by culture supernatants of *P. aeruginosa* PAO-1 (Δ) and PAO-PR1 (O) and by purified toxin A (●).

DETAILED DESCRIPTION OF THE INVENTION THE MICROORGANISM

Figure 1:
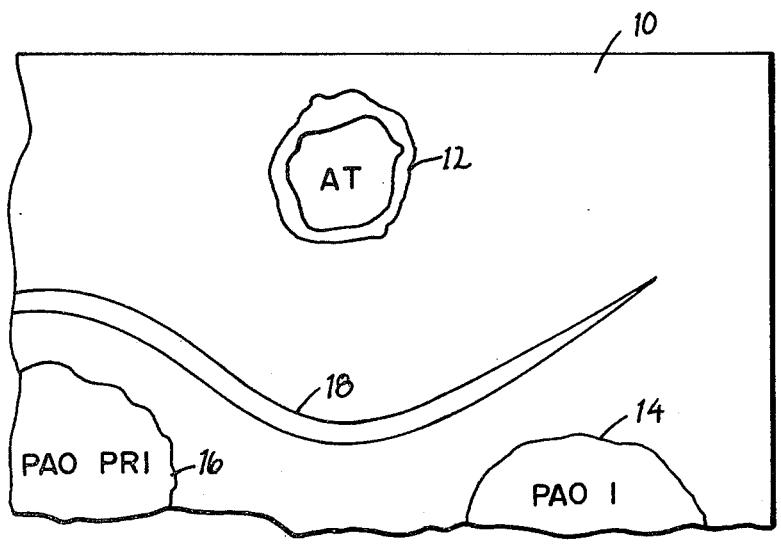

*Pseudomonas aeruginosa* strain PAO-1 has been described in detail in (14). This strain produces toxin A, alkaline protease and elastase and it is virulant in a variety of animal models. *P. aeruginosa* strain PAO-PR1 is derived from strain PAO-1 and is available from the permanent collection of the American Type Culture Collection, 12301 Parklawn Drive, Rockville, Md., 20852, U.S.A., identification ATCC 39018. Cultures of PAO-1 and PAO-PR1 were grown in the trypticase soy broth dialysate (TSBD) medium of Liu (13) which was deferrated by treatment with Chelex 100 chelating resin (minus 400 mesh, Bio-Red Richmond, Calif.) as previously described (15). Specifically, trypticase soy broth was dialyzed, as described in Liu, to produce the dialysate. The dialysate in turn was enriched with the addition of 0.05M monosodium glutamate and 1% glycerol, as described in Bjorn et al. (15). The medium was then deferrated, as described in (15), with the chelating resin.

Strain PAO-PR1 was developed by selecting a PAO-1 strain of *Pseudomonas aeruginosa*, and exposing a culture of this strain to a mutagenic agent. Nontoxic mutant bacterial strains from the mutagenized PAO-1 culture were then isolated, and from among the nontoxic strains, one strain, designated PAO-PR1, was identified which produced a nontoxic toxin A protein which is immunologically crossreactive with the native toxin A protein produced by the PAO-1 strain. The detailed procedure used in developing the PAO-PR1 strain is as follows:

Midlog-phase cells of the PAO-1 strain were harvested by centrigation at 12,000×g for 15 minutes. The cells were washed in 10 ml of buffer (50 mM Tris, 50 mM maleic acid, pH 6.0), then resuspended in 5 ml of the buffer. The chemical mutagen N-methyl-N'-nitrosoguanidine (Sigma) was added to a final concentration of 50 μg/ml. Cultures were incubated for 60 minutes at 32° C., washed twice in deferrated TSBD medium, resuspended in 10 ml of deferrated TSBD medium, and incubated for 20 hours at 32° C. to allow mutant clones to segregate. The above mutagenesis procedure resulted in a decrease of approximately 50% in culture viability (16).

Nontoxic mutagenized culture strains were selected by the Chinese hamster ovary (CHO) cells cytotoxicity assay described by Iglewski and Sadoff (17). To facilitate the screening of a large number of mutagenized clones for nontoxinogenic phenotype, techniques similar to those of Murphy et al. (18) were used. To each well of a conical-bottomed 96-well polystyrene microtiter plate (Linbro/Titertek, Flow Laboratories, Hamden, Conn.) was added 200 μl of deferrated TSBD medium. Single colonies from mutagenized cultures pregrown on nutrient agar (Difco) plates were placed into each well, and the plates were incubated for 20 hours at 32° C. Bacterial cells were then pelleted by centrigation of the microtiter plates for 20 minutes at 2500×g. Approximately 2 μl of culture supernatant was transferred from each microtiter well to a corresponding flat bottomed microtiter well freshly seeded with 2×10$^4$ CHO cells. Plates were incubated for 72 hours at 37° C. in the presence 5% CO$_2$ and scored as previously described (17). Plates containing bacterial cultures were immediately frozen −20° after removal and transfer of supernatant.

Control experiments showed that 2 μl of strain PAO-1 culture supernatant was toxic for CHO cells under the above conditions, and that this toxicity was completely neutralized by the inclusion of specific toxin A antitoxin.

Approximately 22,000 mutagen-treated clones were screened by the CHO cell assay, resulting in the identification of four independently derived mutant strains which displayed a nontoxic phenotype. These four strains were designated PAO-PR1, PAO-A2, PAO-B16, and PAO-C15. The parental strain and four mutant strains were recloned and grown in liquid culture under optimal conditions for toxin A production (16). Cultures were harvested by centrigation at 12,000×g for 15 minutes at 4° C., and the culture supernatant sterilized by membrane filtration.

Culture supernatants from each of the four above-named mutant strains were found to be negative for toxin-induced CHO cell cytotoxicity, as seen in Table I.

The cytotoxicity test is based on the ability of 0.5 μl of culture supernatant to prevent a color change in the CHO cells. Further cytotoxicity tests showed that 0.01 ng native toxin A was toxic for CHO cells, but that 25 ng nontoxic toxin A protein was nontoxic, indicating that native toxin A is at least 2,500 times more toxin in the CHO system than nontoxic toxin A protein.

The culture supernatants from the parental and four nontoxic phenotype strains were also assayed for toxin antigen concentration by liquid phase radioimmunoassay (RIA) for toxin A as described (16). Table I shows that the supernatant concentration of toxin A antigen, expressed as μg/ml, is substantially the same for the PAO-1 (parental) strain and the PAO-PR1 (nontoxic mutant) strain. Supernatants harvested from the other nontoxic strains—PA-A2, PAO-C15, and PAO-B16—contained no detectable levels of toxin A antigen effective to displace radiolabeled toxin A from the toxin A antibody used in the RIA assay. The level of detectability is about 0.5 ng toxin A/ml.

The ADPR-transferase activity of culture supernatants (the ability to ADPR-ribosylate wheat germ EF-2) was determined as previously described (17). Culture supernatants (10 μl per assay) were tested both before and after activation with urea/dithiothreitol. Measured enzyme activity, expressed as counts per minute/10 μl of sample assayed for 30 minutes at 25° C., are shown in Table I. Here it is seen that, of the five strains tested, only the PAO-1 supernatant has measurable ADPR-transferase activity. The level of detectability for this assay is about 0.1 ng. toxin A/ml.

TABLE I

| Bacterial Strain | Toxin-induced CHO cell cytotoxicity | ADPR-transferase activity Unactivated | ADPR-transferase activity Activated | Antigen (ug/ml) |
| --- | --- | --- | --- | --- |
| PAO-1 (Parental) | + | 344 | 21 | 1.02 |
| PAO-A2 | − | 0 | 0 | 0 |
| PAO-C15 | − | 0 | 0 | 0 |
| PAO-B16 | − | 0 | 0 | 0 |
| PAO-PR1 | − | 0 | 0 | 1.16 |

The potentiation of ADPR-transferase activity by urea/dithothreitol in the PAO-1 strain has been discussed (16). Here it is relevant to note only that nontoxic toxin A was enzymatically inactive both in the presence and absence of urea/dithiothreital.

The immunodiffusion characteristics of native and nontoxic toxin A in the PAO-1 and PAO-PR1 supernatants, respectively, were examined by an immunodiffusion technique (16). An agar slab 10 in FIG. 1 has a center wall 12 which contained toxin A antitoxin (AT) and a pair of outer wells 14, 16 which contained toxin from actively growing cell cultures of the parental (PAO-1) and mutant (PAO-PR1) strains, respectively. As seen in the figure, a single band 18 of equal intensity and identity was formed between the mutant and parental strains, indicating antigenic identity between the toxin A proteins produced by the two strains. By contrast, mutant strains PAO-A2, PAO-B15, and PAO-C16 gave no precipitin band in this assay.

Summarizing the data in Table I and in FIG. 1, selection of nontoxic mutant strains from a mutagenized cell culture of P. aeruginosa, strain PAO-1, produced four strains which showed no CHO cell cytotoxicity. Three of these strains—PAO-A2, PAO-C15, and PAO-B16—showed no measurable toxin A antigen, suggesting that these mutant strains are regulatory mutants whose nontoxic phenotype is due to the absence of production or the hypoproduction of toxin A. The PAO-PR1 strain produced an antigenically crossreactive toxin A protein which is characterized below.

The phenotypic stability of strain PAO-PR1 was tested by innoculating 10 ml of deferrated TSBD medium with a single bacterial colony and allowing the cells to grow for 18 hours at 32° C. The culture was diluted and plated for single colonies. A single colony was then used to innoculate fresh medium, and the cycle repeated five times. Ten colonies from the final cycle were selected and grown under conditions for optimal toxin production. Culture supernatants from all of these cultures contained toxin A antigen, but showed no measurable ADPR-transferase activity.

Preparation of Nontoxic Toxin A Protein

Culture conditions for toxin production were as follows: 0.1 ml of an overnight culture (18 hours, 32° C.) was innoculated in 10 ml of deferrated TSBD medium per 250-ml Erlenmeyer flask. Cultures were grown for 20 hours at 32° C. on a reciprocating water bath to give maximal aeration. Cultures were harvested by centrifugation at 12,000×g for 15 min. at 4° C. and were sterilized by membrane filtration.

Toxin A was purified by batch binding to DEAE-cellulose, ammonium sulfate precipitation, and antibody-affinitive chromatography. To 16 L of cell-free supernatant, diluted 1:4 with cold distilled water, was added 600 g. of DEAE-cellulose (Whatman Ltd. Kent, England). The mixture was stirred for 1 hour at 4° C., and then the DEAE-cellulose collected by filtration over Whatman #1 filter paper. The cellulose was washed sequentially with 2 L volumes of buffer A (10 mM Tris (hydroxymethyl amino methane-HCl), 10 mM NaCl, pH 8.0), buffer A containing 50 mM NaCl, and buffer A containing 300 mM NaCl. The toxin A protein eluted in the final wash. Toxin A protein was precipitated with ammonium sulfate (70% saturation) and the redesolved pellet dialyzed against 4 L of 10 mM Tris, pH 8.0. Immunoglobulin G (IgG) from hyperimmune sheep antitoxin was prepared by repeated precipitation of crude antiserum with ammonium sulfate, as previously described (17). Antitoxin IgG was linked to cyanogen bromide activated sepharose 4B (Whatman) by the method of Marsh, et al, (19). Toxin A protein (25 ml. volume) was applied to an antibody-affinity column and eluted with 3M potassium thiocyanate. Nontoxic toxin A protein eluted as a single peak with the salt front. Samples containing toxin A protein were immediately dialyzed against 500 volumes of buffer A and stored at −70° C.

The molecular weight of toxin A produced by PAO-1 was determined by sodium dodecyl sulfate (SDS), polyacrylamide gel electrophoresis (PAGE), performed according to the method of Laemmli (20), as detailed in Cryz, et al (16). As noted earlier the migration rate of nontoxic toxin A in the SDS-PAGE system was substantially identical to that of the native toxin A (16). This result indicates that nontoxic toxin has a molecular weight substantially identical to the known molecular weight of native toxin A of about 66,000 daltons (21).

The purified native and nontoxic toxin A proteins derived from PAO-1 and PAO-PR1 were also examined by agar gel immunodiffusion. With reference again to FIG. 1, the assay was conducted by placing toxin A antitoxin in well 12, and in wells 14, 16, placing native toxin A purified from the parental (PAO-1) strain and nontoxic toxin A purified from the mutant (PAO-PR1) strain, respectively. The results obtained are substantially identical to the results obtained in the immunodiffusion assay of parental and mutant strain supernatants described above. That is, a single precipitin band 18 of equal intensity and identity formed between the purified native and nontoxic toxin A proteins.

Figure 2:
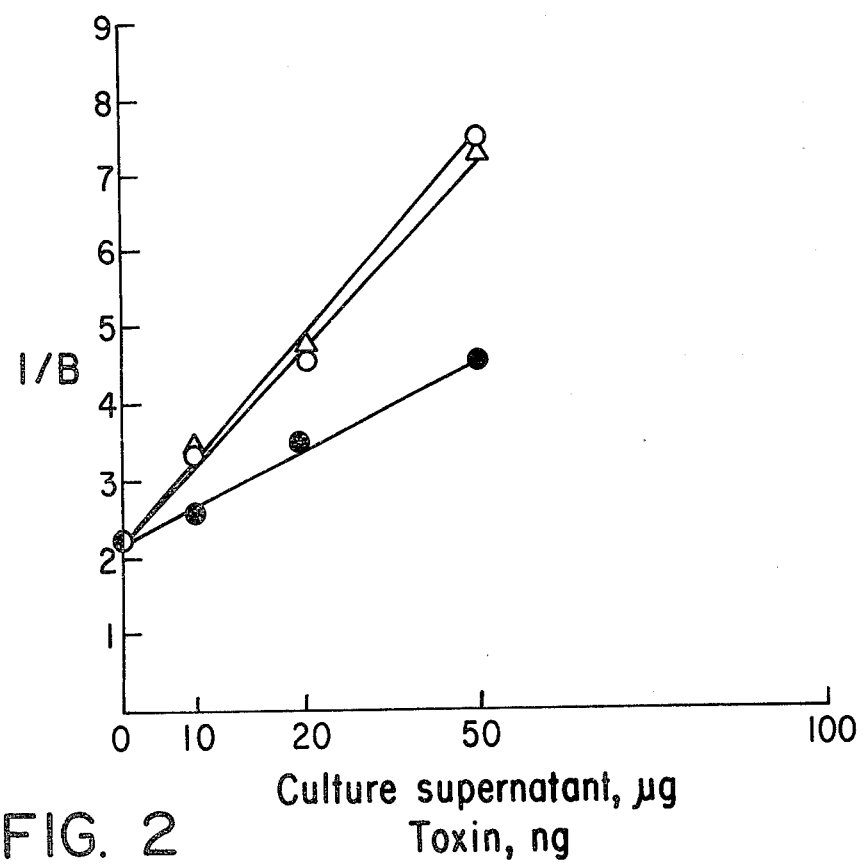

In a liquid phase radioimmunoassay (see above) increasing quantities of culture supernatant from strains PAO-1 and PAO-PR1 which contained nearly identical toxin A antigen concentrations (1.96 and 2.10 ug/ml, respectively) gave superimposable linear displacement curves (FIG. 2). Here the open circles designate PAO-PR1 supernatant, the open triangles, PAO-1 supernatant, and the closed circles, purified toxin A from PAO-PR1. B represents the fraction of radiolabeled toxin A which remains bound after the addition of the indicated ul of cultures supernatant or ng of toxin. Thus, based on their radioimmunoassay, characteristics native and nontoxic toxin A are antigenically indistinguishable.

The ADPR—transferase activities of purified native and nontoxic toxin A proteins were assayed under conditions substantially as described above for assaying cell supernatants. The measured activity of native toxin A, before and after activation with urea/dithiothreitol (22), was 15 and 325 counts per minute per ng protein, respectively. The activity of nontoxic toxin A protein, before and after urea/dithiothreitol activation, was 0.72 and 0.1 counts per minute per ng protein, respectively. Thus, compared with activated native toxin A, activated nontoxic toxin A has substantially no (about 0.03%) APPR—transferase activity.

The nontoxic toxin A protein described herein has been produced directly by mutant strain PAO-PR1 and isolated from the supernatant of a growing cell culture. In view of recently developed recombinant DNA techniques, it is also contemplated that the nontoxic toxin A protein from PAO-PR1 may be derived from a non-PAO-PR1 organism which has received the toxin A gene from PAO-PR1 by recombinant DNA techniques. Thus, it will be understood that the present invention contemplates a nontoxic, immunologically crossreactive toxin A protein which is derived either directly from a PAO-PR1 mutant strain of the type described, or is derived indirectly from another microorganism which contains the toxin A gene present in the PAO-PR1 mutant strain.

Nontoxic Toxin A Protein In Vaccine Use

Several lines of evidence suggest the utility of the nontoxic toxin A protein derived from PAO-PR1 in a vaccine against *P. aeruginosa*. Native toxin A, which is antigenically indistinguishable from nontoxic toxin A, as detailed above, is immunogenic in innoculated animals (22). The antitoxin produced is capable of completely neutralizing the cytotoxicity of PAO-1 in the CHO cell system. The protection afforded by native toxin A antibodies to the morbidity and mortality associated with *P. aeruginosa* has also been studied. Liu and Hsieh (23) first demonstrated that passive immunization of mice with antitoxin A gamma globulin protected mice against the lethality of intraperitoneal infection *P. aeruginosa*. Pavlovskis, et al. (6), and Snell et al. (24) observed that passive immunization of mice with specific antitoxin increased the survival of burned mice infected with toxigenic strains as compared to control mice. Combining antibiotic therapy (gentamycin) with passive antitoxin therapy may provide additional protection against Pseudomonas infections in some systems (24).

Nontoxic toxin A is immunogenic in animals infected with PAO-PR1. Chronic lung infections in rats infected with PAO-1 and PAO-PR1, respectively, resulted in the elicitation of comparable high CHO cell-neutralizing antitoxin titers. The toxin A antitoxin derived from PAO-PR1 infected rats was also shown to be immunologically indistinguishable, in immunodiffusionassay, from the toxin A antitoxin produced by rats infected with the PAO-1 strain. Thus, native and nontoxic toxin A appear to elicit identical toxin A antibodies in animals challenged with either the PAO-1 or PAO-PR1 strain.

Neither active nor passive immunization of humans against toxin A has yet been reported. However, a number of studies have demonstrated antibody to toxin A in human serum (25, 26). Human toxin A antibody titers have been shown to increase with Pseudomonas bacteremia (26, 27) and initial high titers of antibody to toxin A have correlated with improved prognosis in bacteremia patients (27). More recently, Cross et al (7) reported that patients who survived and those who died of bacteremia from toxin A-producing Pseudomonas strains had mean peak levels of antitoxin IgG of $25.8 \pm 5.5$ and $4.6 \pm 2.0$ μg/ml, respectively. These data suggest that toxin A contributes significantly to the morbidity and mortality of *P. aeruginosa* bacteremia, and that specific toxin A antibodies are protective.

Nontoxic toxin A has been found to be at least 100 times less toxic than toxin A when innoculated in mice and is at least 2,500 less toxic in the CHO system. Therefore, nontoxic toxin A is expected to be safe when innoculated in animals and humans in passive and active immunization. Antibodies produced against the nontoxic toxin A protein in the rat lung model appear to be immunologically indistinguishable from native toxin A antibodies, which have shown to confer passive immunization protection in *P. aeruginosa* infected animal systems. Finally, the correlation between toxin A antibody levels and mortality rate in humans with *P. aeruginosa* bacteremia indicates that antitoxin formed by active or passive immunization with nontoxic toxin A protein will provide protection against *P. aeruginosa* infections in humans.

While a preferred embodiment of the invention has been described herein, it will be obvious to those skilled in the art that various changes and modifications may be made without departing from the spirit of the invention.

It is claimed and desired to secure by Letters Patent:

1. A purified nontoxic, immunologically crossreactive toxin A protein derived from a PAO-PR1 mutant strain of *Pseudomonas aeruginosa*, having the identifying characteristics of ATCC 39018.

2. The protein of claim 1, having substantially no ADPR-transferase activity in its activated form.

3. The protein of claim 1, having a molecular weight of about 66,000 daltons.

4. The protein of claim 1, which is immunologically indistinguishable, based on its immunodiffusion and radioimmunoassay characteristics, from native toxin A protein derived from a PAO-1 strain of *Pseudomonas aeruginosa*.

5. A purified nontoxic toxin A protein produced by a microorganism of the strain *Pseudomonas aeruginosa* PAO-PR1 (ATCC 39018) and having the characteristics of
(1) a molecular weight of about 66,000 daltons,
(2) immunologically indistinguishable, based on its immunodiffusion and radioimmunoassay characteristics, from native toxic toxin A protein produced by a microorganism of the strain *Pseudomonas aeruginosa* PAO-1, and
(3) substantially no ADPR-transferase activity in its activated form.

* * * * *